(12) United States Patent
Field et al.

(10) Patent No.: US 8,568,334 B2
(45) Date of Patent: *Oct. 29, 2013

(54) CORE BIOPSY DEVICE

(75) Inventors: Steven E. Field, Grand Rapids, MI (US);
Stephen F. Peters, Hickory Corners, MI (US); Brian R. Mulder, Rockford, MI (US); Michael Johnson, West Olive, MI (US); Todd Ireland, Coopersville, MI (US); Steve Haeske, Allendale, MI (US); Mark Vander Veen, Hudsonville, MI (US)

(73) Assignee: Inrad, Inc., Grand Rapids, MI (US)

( * ) Notice: Subject to any disclaimer, the term of this patent is extended or adjusted under 35 U.S.C. 154(b) by 621 days.

This patent is subject to a terminal disclaimer.

(21) Appl. No.: 12/209,360

(22) Filed: Sep. 12, 2008

(65) Prior Publication Data

US 2009/0012423 A1    Jan. 8, 2009

Related U.S. Application Data

(63) Continuation of application No. 11/939,617, filed on Nov. 14, 2007, now abandoned, and a continuation-in-part of application No. 10/908,427, filed on May 11, 2005, now Pat. No. 8,088,081.

(60) Provisional application No. 60/521,518, filed on May 11, 2004.

(51) Int. Cl.
*A61B 10/00*     (2006.01)
*A61B 17/32*     (2006.01)

(52) U.S. Cl.
USPC .......................................... 600/567; 606/170

(58) Field of Classification Search
USPC .......... 600/562–568, 570, 571; 606/167, 170, 606/171
See application file for complete search history.

(56) References Cited

U.S. PATENT DOCUMENTS

| 3,007,471 | A | 11/1961 | McClure, Jr. |
| 4,368,734 | A | 1/1983 | Banko |
| 4,651,752 | A | 3/1987 | Fuerst |
| 4,708,147 | A | 11/1987 | Haaga |
| 4,735,215 | A | 4/1988 | Goto et al. |
| 4,776,346 | A | 10/1988 | Beraha et al. |
| 4,781,202 | A | 11/1988 | Janese |
| 4,881,551 | A | 11/1989 | Taylor |
| 4,893,635 | A | 1/1990 | de Groot et al. |
| 4,924,878 | A | 5/1990 | Nottke |
| 4,926,877 | A | 5/1990 | Bookwalter |
| 4,958,625 | A | 9/1990 | Bates et al. |
| 5,036,860 | A | 8/1991 | Leigh et al. |
| 5,090,419 | A | 2/1992 | Palestrant |

(Continued)

FOREIGN PATENT DOCUMENTS

| CA | 1185491 | 4/1985 |
| DE | 20010879 | 10/2000 |

(Continued)

*Primary Examiner* — Max Hindenburg
*Assistant Examiner* — John Pani
(74) *Attorney, Agent, or Firm* — McGarry Bair

(57) ABSTRACT

A core biopsy device comprises a cutting cannula provided at a distal end with a helical excising blade. The cutting cannula can be rotated within a tissue mass so that the helical excising blade can excise a biopsy sample from the surrounding tissue.

22 Claims, 12 Drawing Sheets

(56) References Cited

U.S. PATENT DOCUMENTS

| | | | |
|---|---|---|---|
| 5,111,828 | A | 5/1992 | Kornberg et al. |
| 5,133,360 | A | 7/1992 | Spears |
| 5,133,713 | A | 7/1992 | Huang et al. |
| RE34,056 | E | 9/1992 | Lindgren et al. |
| 5,156,160 | A | 10/1992 | Bennett |
| 5,161,542 | A | 11/1992 | Palestrant |
| 5,183,054 | A | 2/1993 | Burkholder et al. |
| 5,188,118 | A | 2/1993 | Terwilliger |
| 5,195,533 | A | 3/1993 | Chin et al. |
| 5,197,484 | A | 3/1993 | Kornberg et al. |
| 5,224,488 | A | 7/1993 | Neuffer |
| 5,249,583 | A | 10/1993 | Mallaby |
| 5,251,641 | A | 10/1993 | Xavier |
| 5,353,804 | A | 10/1994 | Kornberg et al. |
| 5,368,045 | A | 11/1994 | Clement et al. |
| 5,375,608 | A | 12/1994 | Tiefenbrun et al. |
| 5,462,062 | A | 10/1995 | Rubinstein et al. |
| 5,477,862 | A | 12/1995 | Haaga |
| 5,546,957 | A | 8/1996 | Heske |
| 5,634,473 | A | 6/1997 | Goldenberg et al. |
| 5,655,542 | A | 8/1997 | Weilandt |
| 5,709,697 | A | 1/1998 | Ratcliff et al. |
| 5,752,923 | A | 5/1998 | Terwilliger |
| 5,779,647 | A | 7/1998 | Chau et al. |
| 5,788,651 | A | 8/1998 | Weilandt |
| 5,807,277 | A | 9/1998 | Swaim |
| 5,810,806 | A | 9/1998 | Ritchart et al. |
| 5,827,305 | A | 10/1998 | Gordon |
| 5,842,999 | A | 12/1998 | Pruitt et al. |
| 5,857,982 | A | 1/1999 | Milliman et al. |
| 5,882,316 | A | 3/1999 | Chu et al. |
| 5,910,121 | A | 6/1999 | Paolo et al. |
| 5,913,857 | A * | 6/1999 | Ritchart et al. ................ 606/45 |
| 5,928,162 | A | 7/1999 | Giurtino et al. |
| 5,951,489 | A | 9/1999 | Bauer |
| 5,961,534 | A | 10/1999 | Banik et al. |
| 5,989,196 | A | 11/1999 | Chu et al. |
| 5,989,197 | A | 11/1999 | Avaltroni |
| 5,993,399 | A | 11/1999 | Pruitt et al. |
| 6,007,495 | A | 12/1999 | Matula |
| 6,007,497 | A | 12/1999 | Huitema |
| 6,019,733 | A | 2/2000 | Farascioni |
| 6,027,458 | A * | 2/2000 | Janssens ................ 600/567 |
| 6,050,955 | A | 4/2000 | Bryan et al. |
| 6,083,237 | A | 7/2000 | Huitema et al. |
| 6,136,014 | A | 10/2000 | Sirimanne et al. |
| 6,142,955 | A | 11/2000 | Farascioni et al. |
| 6,165,136 | A | 12/2000 | Nishtala |
| 6,176,834 | B1 | 1/2001 | Chu et al. |
| 6,193,673 | B1 | 2/2001 | Viola et al. |
| 6,248,081 | B1 | 6/2001 | Nishtalas et al. |
| 6,273,862 | B1 | 8/2001 | Privitera et al. |
| 6,293,945 | B1 | 9/2001 | Parins et al. |
| 6,395,011 | B1 | 5/2002 | Johanson et al. |
| 6,416,484 | B1 | 7/2002 | Miller et al. |
| 6,432,064 | B1 | 8/2002 | Hibner et al. |
| 6,436,054 | B1 | 8/2002 | Viola et al. |
| 6,443,910 | B1 | 9/2002 | Krueger et al. |
| 6,488,636 | B2 | 12/2002 | Bryan et al. |
| 6,517,498 | B1 | 2/2003 | Burbank et al. |
| 6,551,254 | B2 | 4/2003 | Nishtalas et al. |
| 6,554,779 | B2 | 4/2003 | Viola et al. |
| 6,569,176 | B2 | 5/2003 | Jessep |
| 6,610,020 | B2 | 8/2003 | Voegele |
| 6,620,111 | B2 | 9/2003 | Stephens et al. |
| 8,088,081 | B2 * | 1/2012 | Field et al. ................ 600/567 |
| 2001/0011156 | A1 | 8/2001 | Viola et al. |
| 2002/0045842 | A1 | 4/2002 | Van Bladel et al. |
| 2003/0153843 | A1 | 8/2003 | Nishtalas et al. |
| 2004/0019299 | A1 | 1/2004 | Ritchart et al. |
| 2006/0030785 | A1 * | 2/2006 | Field et al. ................ 600/567 |
| 2007/0016101 | A1 * | 1/2007 | Feldman et al. ................ 600/567 |

FOREIGN PATENT DOCUMENTS

| | | |
|---|---|---|
| EP | 0852127 A1 | 7/1998 |
| EP | 1252863 A1 | 10/2002 |
| SU | 1537232 A1 | 1/1990 |
| WO | 9508291 | 3/1995 |
| WO | 9508292 | 3/1995 |
| WO | 9508946 | 4/1995 |
| WO | 9726835 | 7/1997 |
| WO | 03077767 A1 | 9/2003 |

* cited by examiner ced to sever the tissue mass. Since the sample normally comprises wetted tissue that completely fills the coring cannula, the suction force and/or the frictional force between the tissue sample and the inner wall of the coring cannula are the dominate forces for retaining the sample in the cannula. However, if these forces are not sufficient to tear the end of the sample from the tissue mass, the sample will be pulled out of the coring cannula upon the removal of the coring cannula. Some practitioners pivot the biopsy device in hopes that the end of the cannula will at least partially sever the attached portion of the sample. However, this is not preferred as it increases the damage to the remaining tissue.

CORE BIOPSY DEVICE

CROSS-REFERENCE TO RELATED APPLICATION(S)

This application is a continuation of U.S. patent application Ser. No. 11/939,617, filed Nov. 14, 2007, now abandoned, and a continuation-in-part of U.S. patent application Ser. No. 10/908,427, filed May 11, 2005, now U.S. Pat. No. 8,088,081, issued Jan. 3, 2012, which claims the benefit of U.S. Provisional Application No. 60/521,518, filed May 11, 2004, all of which are incorporated herein by reference in their entirety.

BACKGROUND OF THE INVENTION

It is frequently necessary to sample or remove a sample from a suspect tissue for testing. In humans, such a sample removal is particularly useful in diagnosis and treatment of cancerous or pre-cancerous conditions. In the case of suspected cancer, particularly cancer of the breast, early detection and diagnosis is critical to the success of the patient's treatment and recovery.

Various techniques are available to aid in detection and diagnosis, including physical examination and imaging, such as mammography, x-ray, ultrasound, magnetic resonance imaging (MRI), and the like. When a condition is detected that suggests the possibility of cancer, a biopsy can be performed to obtain tissue samples for a complete diagnosis.

One biopsy technique frequently performed is a core biopsy, which uses a core biopsy device in which a cannula is inserted into the tissue of interest, thereby coring a biopsy sample from the tissue having a cross section similar to that of the cannula, and which is retained within the cannula. The cannula, with the biopsy sample, is then removed from the tissue, followed by cytological and/or histological analysis of the sample.

One group of core biopsy devices is based on the combination of a notched inner stylet and an outer severing cannula. The stylet is retained within the lumen of the outer cannula such that the pointed end of the stylet closes off the open end of the cannula. The stylet and cannula are advanced into the tissue mass until they are near the desired biopsy site. The stylet is then advanced relative to the outer cannula to expose the notch to the biopsy site where the tissue prolapses into the notch. The outer cannula is then advanced to sever the tissue in the notch. The disadvantage of this method is that it produces a small core biopsy relative to the outer cannula size since the cross section of the sample is substantially smaller than the cross section of the outer cannula. The advantage of this method is that the sample is completely severed from the tissue mass and securely retained within the notch.

Another group of core biopsy devices is based on a coring cannula in combination with a non-notched stylet. The stylet is used to plug the end of the coring cannula during the insertion of the coring cannula into the tissue adjacent the biopsy site. The coring cannula is then advanced relative to the stylet into the biopsy site to retain a sample within the coring cannula. The advantage of this device is that a full core biopsy sample is obtained. That is, the cross section of the sample is substantially equal to the cross section of the coring cannula. The full core sample provides a much larger sample which is highly advantageous.

The disadvantage of this full core biopsy device is that the end of the sample is not positively severed from the tissue mass, creating the possibility that the biopsy sample will be pulled out of the coring cannula upon the withdrawal of the coring cannula. This can happen if the forces holding the sample in the coring cannula are not sufficient to tear the end of the sample from the tissue mass. Since the sample normally comprises wetted tissue that completely fills the coring cannula, the suction force and/or the frictional force between the tissue sample and the inner wall of the coring cannula are the dominate forces for retaining the sample in the cannula. However, if these forces are not sufficient to tear the end of the sample from the tissue mass, the sample will be pulled out of the coring cannula upon the removal of the coring cannula. Some practitioners pivot the biopsy device in hopes that the end of the cannula will at least partially sever the attached portion of the sample. However, this is not preferred as it increases the damage to the remaining tissue.

Another disadvantage of all of the full core devices is that they rely on the relative movement between the coring cannula and the stylet to expel the sample from the interior of the coring cannula. The use of the stylet to force out the sample can damage the sample. The damage can be great enough to render the sample unsuitable for testing. This can be very detrimental since some lesions being sampled are small enough that the entire lesion is contained within the sample. For larger lesions, some practitioners will take multiple samples to allow for potential damage of one of the samples. This practice increases the invasiveness of the procedure and the pain to the patient.

While there have been many attempts in the art to produce a workable core biopsy device, there is still a strong need for a core biopsy device that minimizes patient discomfort, insures a complete excision of the biopsy sample from the surrounding tissue, enables the biopsy sample to be removed from the device without disturbance of the sample, and is simple and cost effective to manufacture.

SUMMARY OF THE INVENTION

The invention relates to a method and apparatus for the percutaneous removal of a specimen from a tissue mass. The biopsy apparatus comprises a cannula defining a lumen and a longitudinal axis. The cannula has a proximal end and a distal end, with a helical excising finger extending from the distal end. An actuator is operably coupled to the cannula for rotating the helical excising finger to sever the specimen from the tissue mass.

DESCRIPTION OF AN EMBODIMENT OF THE INVENTION

Figure 1:
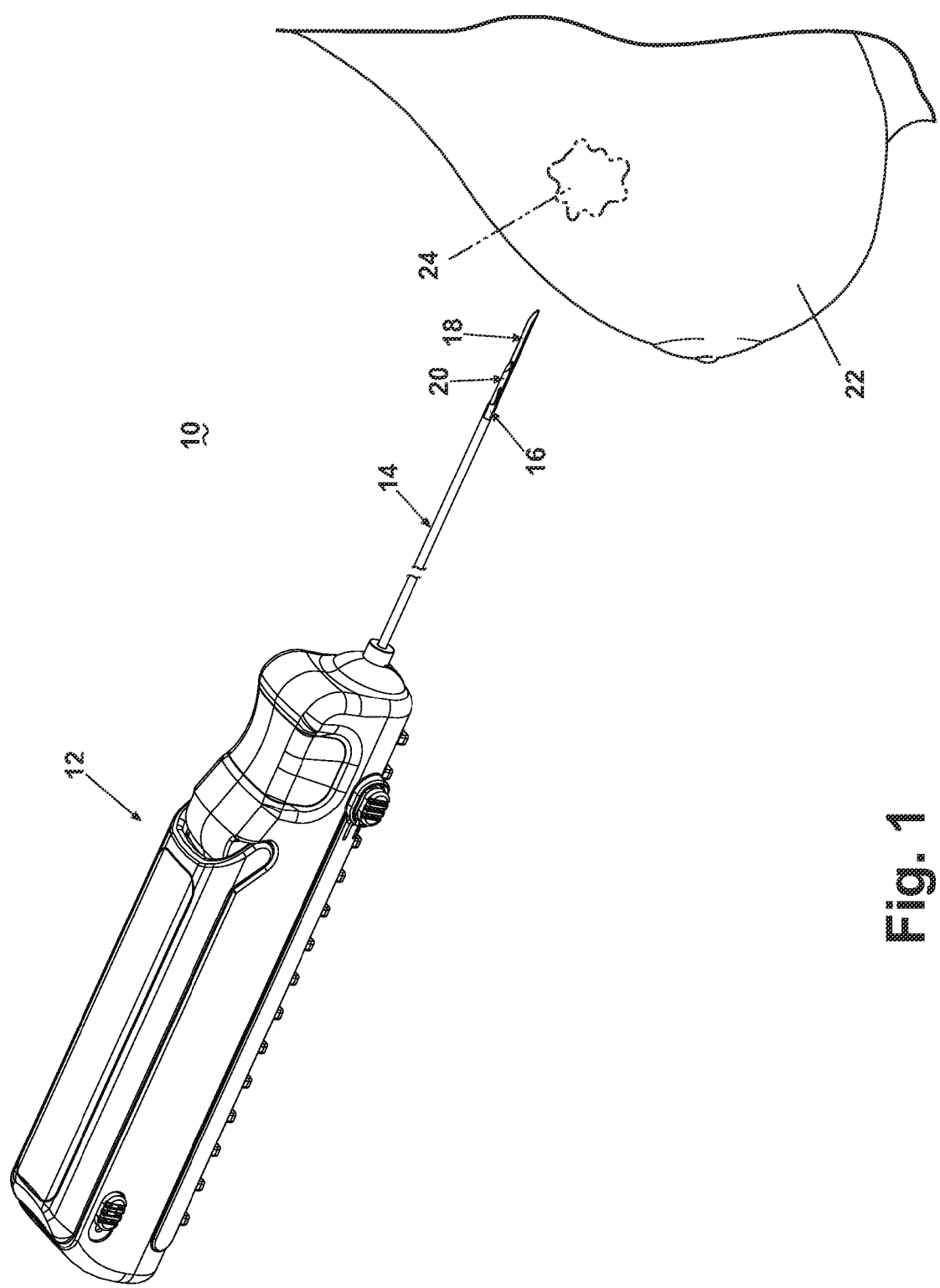
FIG. 1 is a perspective view of a lesion within a tissue mass and a first embodiment of a core biopsy device comprising an actuator assembly and a cannula assembly according to the invention for obtaining a core biopsy sample from the lesion.

Referring now to the drawings, and specifically to FIG. 1, a core biopsy device 10 is illustrated comprising an actuator assembly 12 structurally and operably connected to a cannula assembly 14. The cannula assembly 14 is utilized to penetrate a tissue mass 22 for obtaining a core biopsy sample from a lesion 24 as more specifically described hereinafter. An embodiment of the actuator assembly 12 is described and illustrated herein comprising an automated, integrated hand-held device capable of controlling the acquisition and removal of the core biopsy sample from the lesion 24. An actuator assembly 12 is preferably utilized that is capable of automated firing of the cannula assembly 14, with the additional capability of firing a pair of telescoping cannulae and a stylet with one triggering action, or firing an inner cannula and an outer cannula independently. As described and illustrated herein, the actuator assembly 12 is capable of controlled rotation of the outer cannula around the inner cannula after the cannulae have been fired to excise the core biopsy sample from the surrounding lesion 24. A suitable actuator assembly 12 is more fully described in U.S. patent application Ser. No. 10/908,427, filed May 11, 2005, now U.S. Pat. No. 8,088,081, issued Jan. 3, 2012, which is incorporated herein by reference in its entirety.

The actuator assembly 12 will not be described in greater detail as the type of actuator assembly is not germane to the invention. The actuator assembly need only be able to effect the movement of the cannulae as described herein to effect the taking of the specimen. As such an actuator assembly is known in the art, no further description is warranted.

Figure 2:
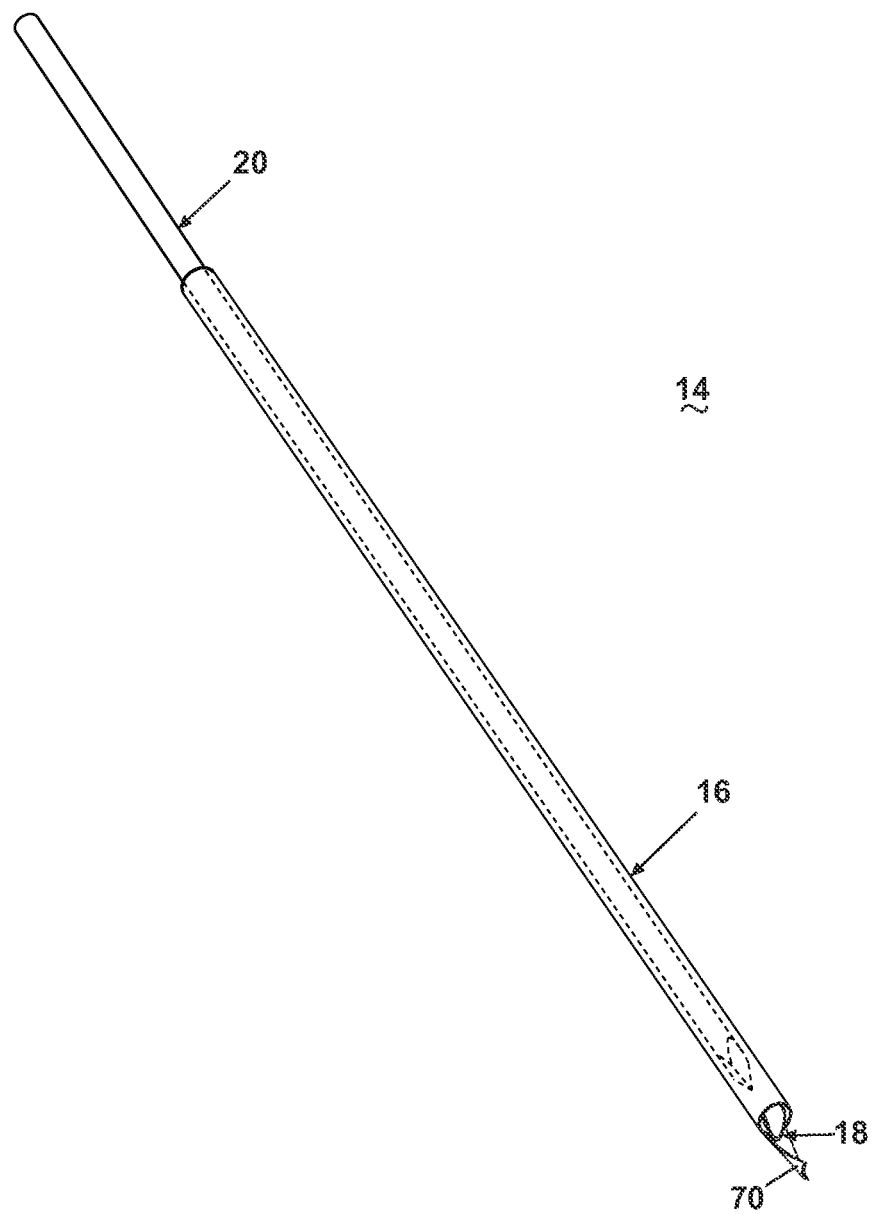
FIG. 2 is a perspective view of a cannula assembly comprising a coring cannula, a spoon cannula, and a stylet, with the coring cannula in an excising position.
Figure 3:
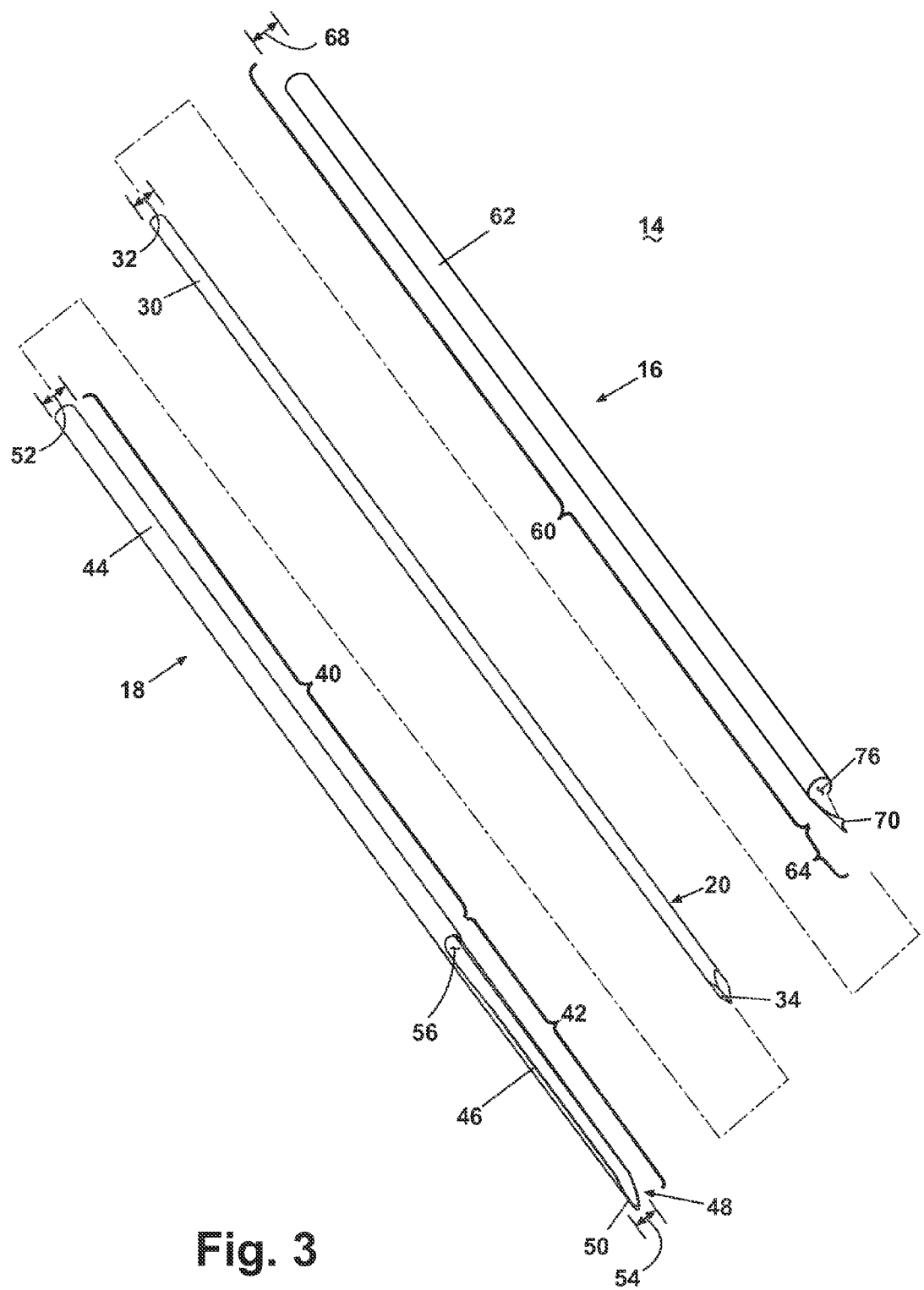
FIG. 3 is an exploded view of the coring cannula, spoon cannula, and stylet comprising the cannula assembly illustrated in FIG. 2.

Referring now to FIGS. 2-6, the cannula assembly 14 comprises a coring cannula 16, a spoon cannula 18, and a stylet 20 in coaxially telescoping relationship, as illustrated in FIGS. 2 and 3. As used herein with respect to the coring cannula 16, the spoon cannula 18, and the stylet 20, the terms "distal" and "forward" refer to or in a direction toward that end of the cannulae 16, 18 and/or the stylet 20 that is directed toward the lesion 24 and away from the actuator assembly 12. "Proximal" or "rearward" thus refers to or in a direction toward that end of the cannulae 16, 18 and/or the stylet 20 that is directed away from the lesion 24 and toward the actuator assembly 12. Preferably, the coring cannula 16, the spoon cannula 18, and the stylet 20 are fabricated of a well-known surgically suitable material, such as stainless steel.

Figure 4:
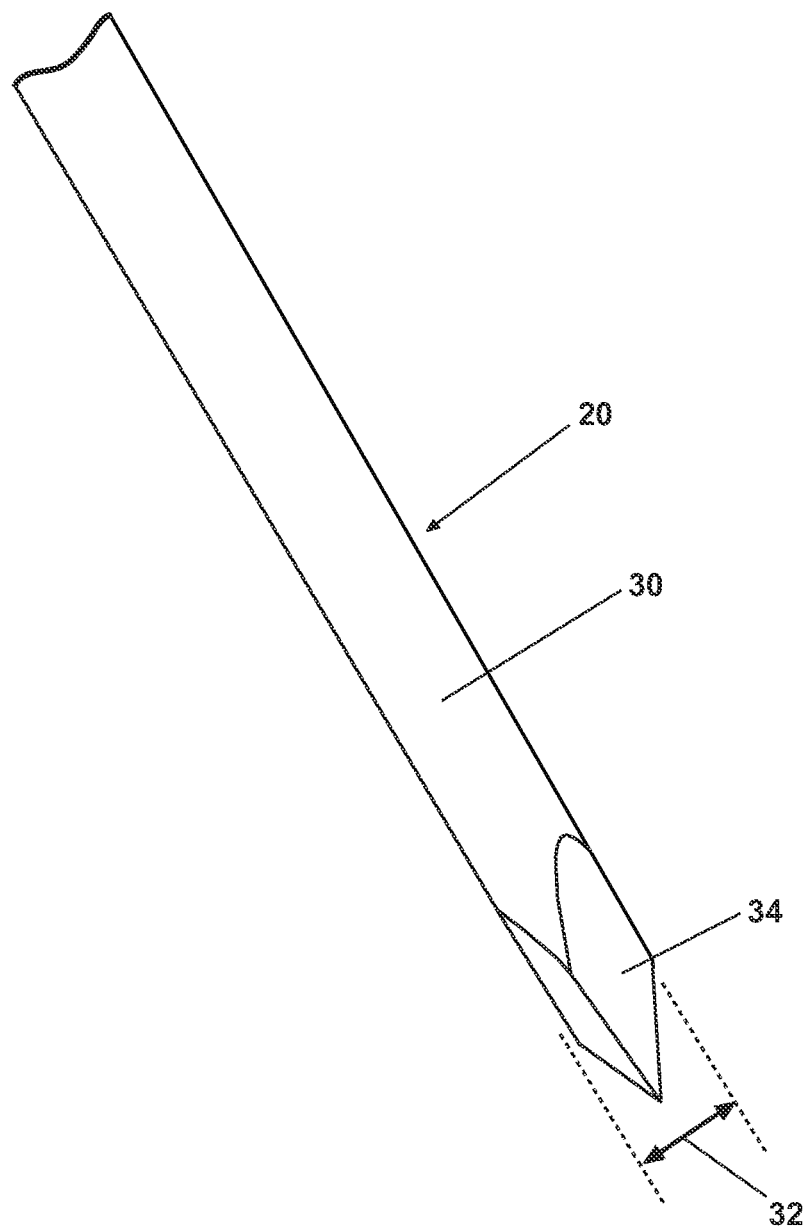
FIG. 4 is an enlarged perspective view of a distal end of the stylet illustrated in FIG. 3.

Referring specifically to FIG. 4, the stylet 20 is an elongated, solid cylindrical member comprising a well-known stylet body 30 terminating in a pointed penetration tip 34. The stylet body 30 has a constant stylet diameter 32 which is sized for slidable and coaxial insertion through the spoon cannula 18.

Figure 5:
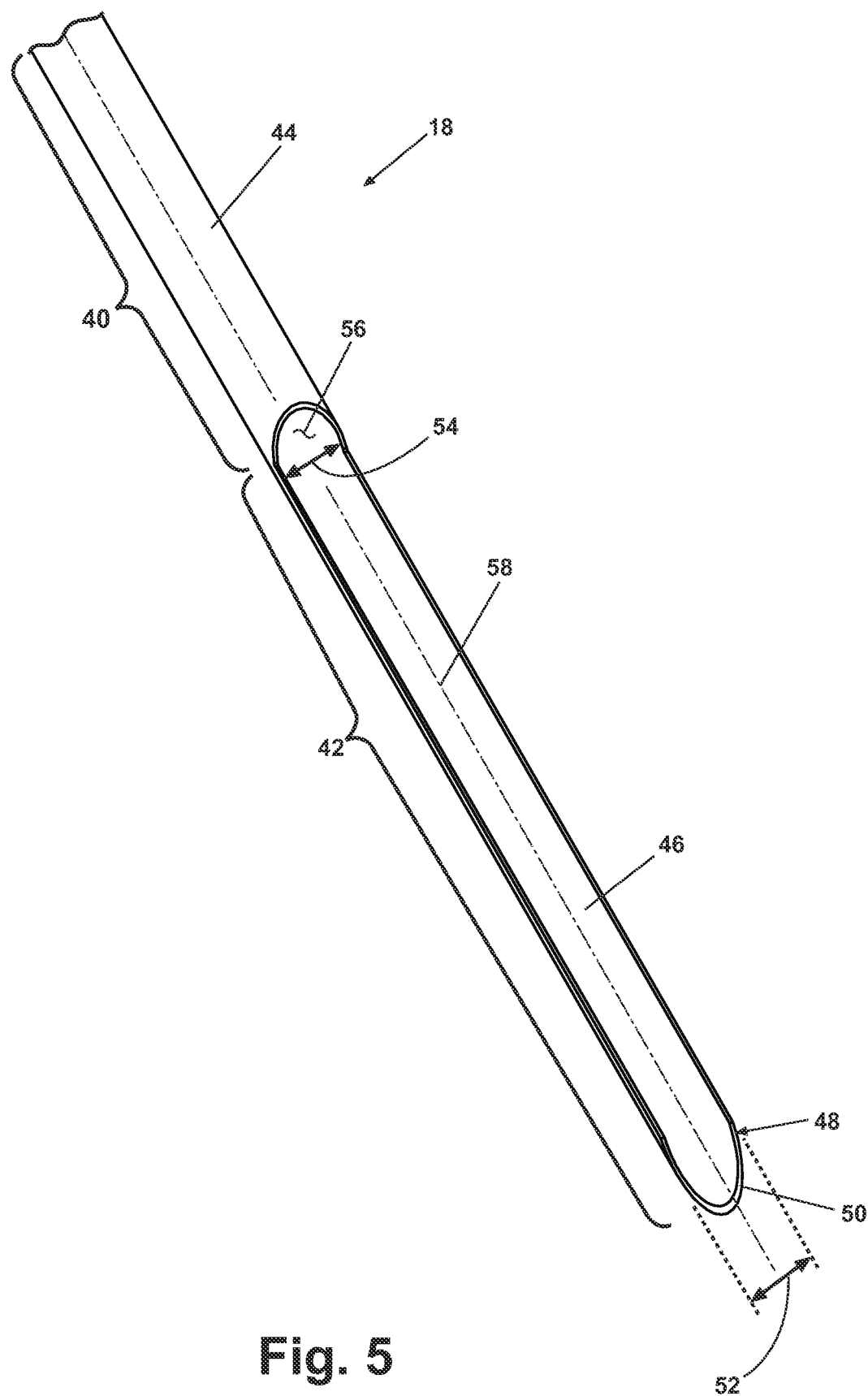
FIG. 5 is an enlarged perspective view of a distal end of the spoon cannula illustrated in FIG. 3.

Referring specifically to FIG. 5, the spoon cannula 18 is an elongated, tubular member having an enclosed section 40 smoothly transitioning distally to a spoon section 42. The enclosed section 40 comprises an annular wall 44 having an outer diameter 52 defining a lumen 56 having an inner diameter 54. The spoon section 42 comprises an arcuate wall 46 contiguous with a portion of the annular wall 44. The arcuate wall 46 is preferably semicircular, defining a central angle of 180°. Alternatively, the arcuate wall 46 can comprise an arc length defining a central angle ranging between about 120° and somewhat greater than 180°. An arc length greater than 180° will provide enhanced support of the biopsy sample and will minimize the risk of unintended sample deformation during removal of the sample from the spoon section 42. The inner diameter 54 is somewhat greater than the stylet diameter 32 so that the stylet 20 is slidably received within the lumen 56.

The arcuate wall 46 terminates at a distal end in an insertion tip 48. The distal edge of the arcuate wall 46 at the insertion tip 48 is inclined relative to a longitudinal axis 58 of the spoon cannula 18 to define a parabolic beveled edge 50. The beveled edge 50 can be provided with a secondary bevel, which in effect sharpens the beveled edge 50, to enhance the penetration capability of the spoon cannula 18 into the tissue mass 22 and the lesion 24.

Figure 6:
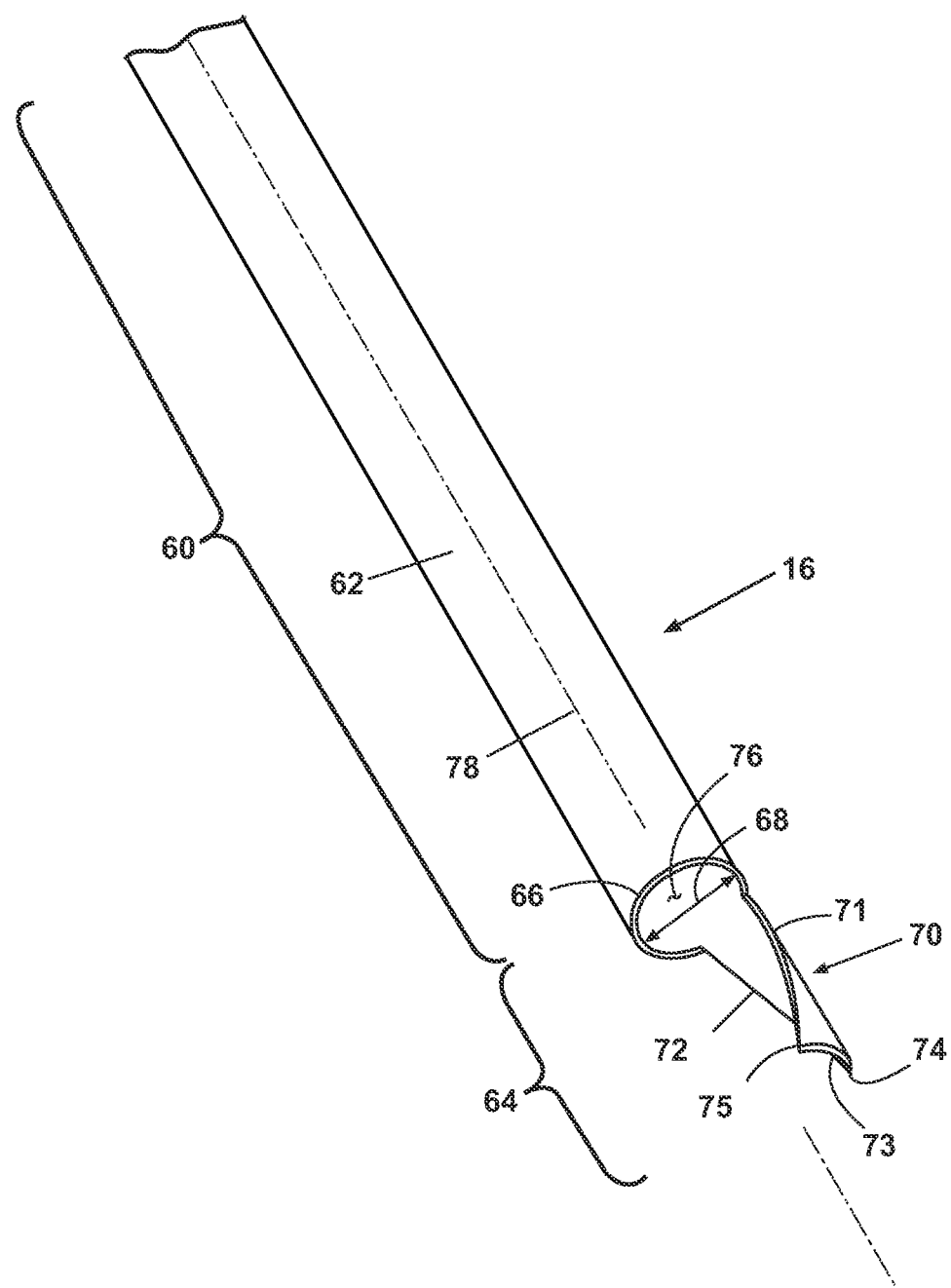
FIG. 6 is an enlarged perspective view of a distal end of the coring cannula illustrated in FIG. 3.

The coring cannula 16, illustrated specifically in FIG. 6, is an elongated, tubular member having an enclosed section 60 comprising an annular wall 62 defining a lumen 76 therethrough having an inner diameter 68. The coring cannula 16 terminates at a distal end in a cutting tip 64. The cutting tip 64 is generally perpendicular to a longitudinal axis 78 of the coring cannula 16 to define a circular beveled edge 66. The beveled edge 66 can be provided with a secondary bevel, which in effect sharpens the beveled edge 66, to enhance the penetration capability of the coring cannula 16 into the tissue mass 22 and the lesion 24.

The inner diameter 68 of the coring cannula 16 is somewhat greater than the outer diameter 52 of the spoon cannula 18 so that the spoon cannula 18 is slidably received within the lumen 76 of the coring cannula 16.

The cutting tip 64 transitions at a distal end to a helical excising finger 70 extending generally longitudinally away from the cutting tip 64. The helical excising finger 70, illustrated in detail in FIG. 7, comprises a curved surface formed into a helical shape, with a pair of opposed lateral edges 71, 72 terminating in a distal edge 73 having corners 74, 75 formed by the junction of the lateral edges 71, 72 and the distal edge 73. The lateral edges 71, 72 curve around the longitudinal axis 78. In one exemplary embodiment, the lateral edges 71, 72 can have a constant curvature, each making a circular helix. The helical excising finger 70 could alternately have lateral edges 71, 72 that curve along an imaginary cone, so that each lateral edge 71, 72 makes a conical helix.

The edges 71, 72, 73 can be beveled to enhance the penetration and cutting characteristics of the helical excising finger 70. The distal edge 73 can alternately comprise a pointed tip to enhance the penetration and cutting characteristics of the excising finger 70. The helical excising finger 70 is adapted to have a resilience which enables the helical excising finger 70 to elastically deflect away from the longitudinal axis 78 and to return to an at-rest helical configuration as best seen in FIG. 7.

Figure 7:
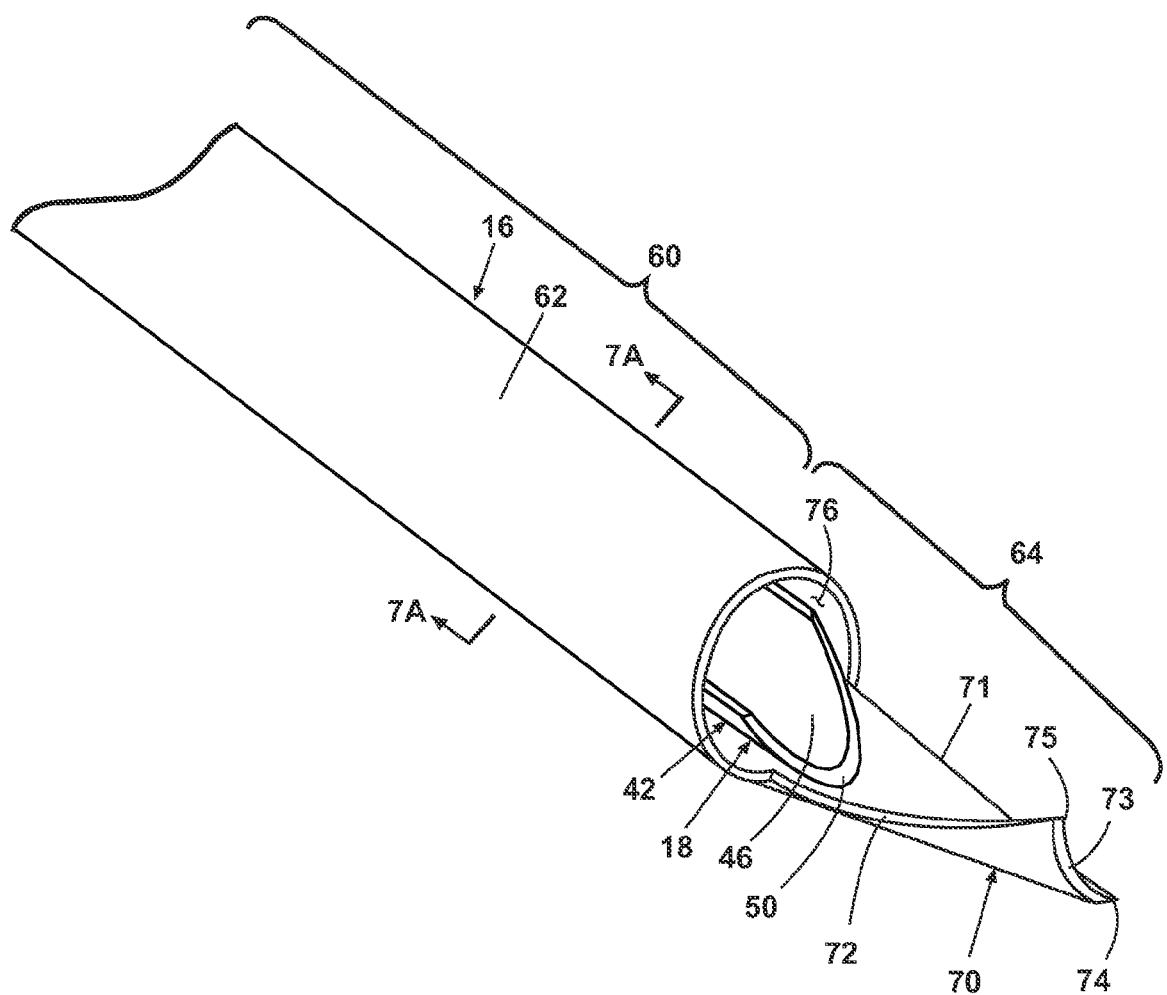
FIG. 7 is an enlarged view of a distal end of the coring cannula and the spoon cannula telescopically received therein, with the coring cannula in the excising position.
Figure 7A:
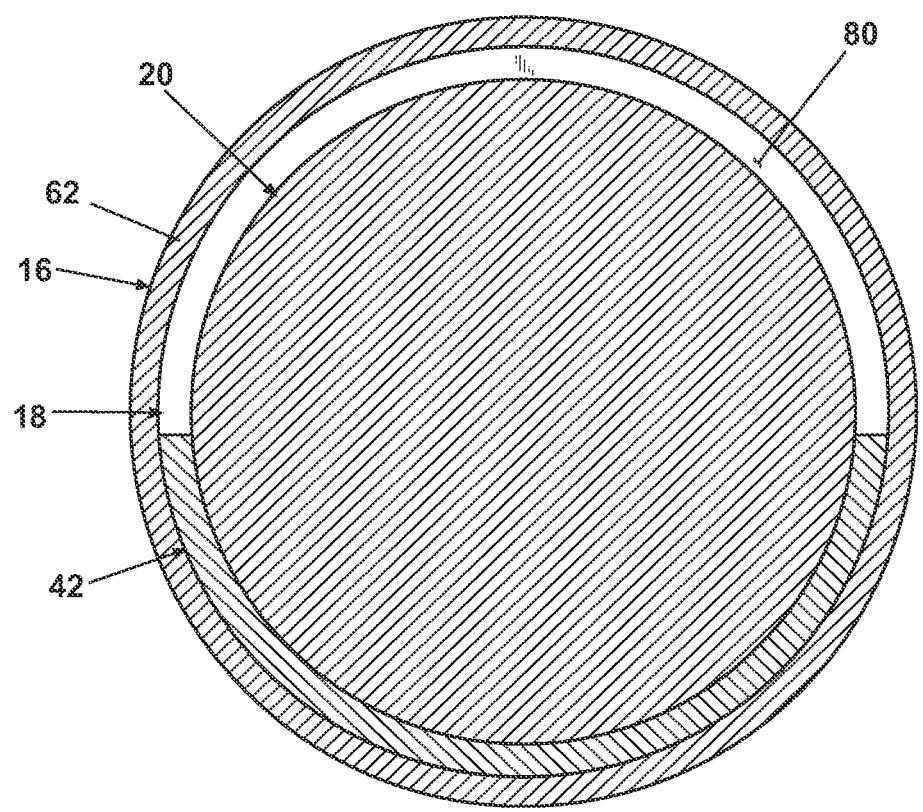
FIG. 7A is a sectional view taken along view line 7A-7A of FIG. 7.

As illustrated in FIG. 7A, the semi-circular configuration of the spoon section 42 results in a semi-annular gap 80 being defined between the stylet 20 and the annular wall 62 of the coring cannula 16 when the coring cannula 16, the spoon cannula 18, and the stylet 20 are in telescoping relationship. This gap 80 extends longitudinally from the insertion tip 48 to the enclosed section 40.

Figure 8A:
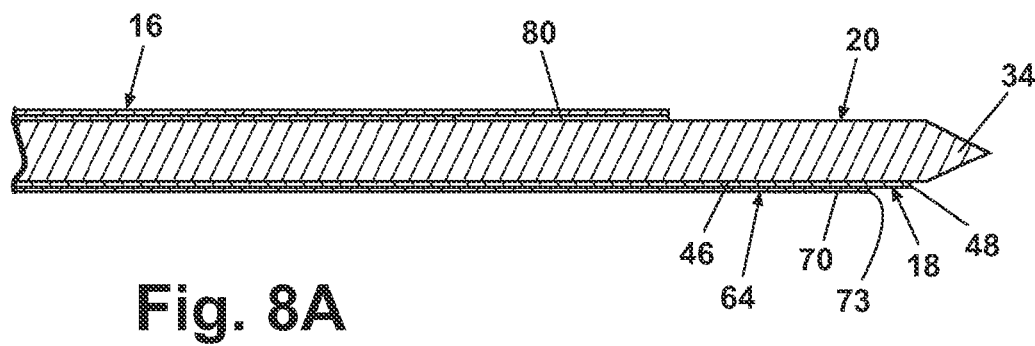
FIG. 8A is a longitudinal section view illustrating the cannula assembly in a "cocked" configuration ready for an insertion into the tissue mass.
Figure 8B:
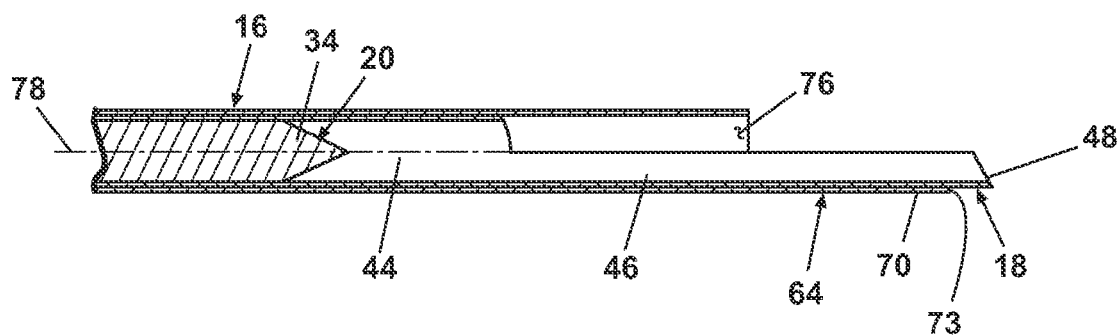
FIG. 8B is a longitudinal sectional view illustrating the cannula assembly in a sampling configuration with the coring cannula and the spoon cannula projected distally over the stylet.
Figure 8C:
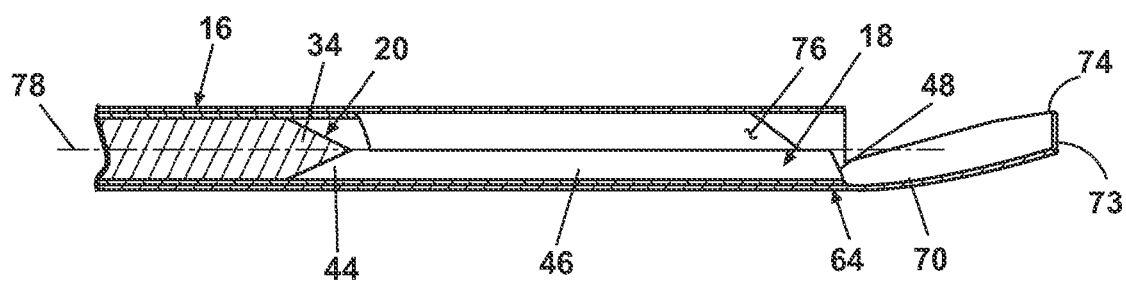
FIG. 8C is a longitudinal sectional view illustrating the cannula assembly in a sample excising configuration with the coring cannula extending distally of the spoon cannula.

As illustrated in FIGS. 6, 7, and 8C, the helical excising finger 70 is curved inwardly around the longitudinal axis 78 so that the distal edge 73 extends to, and preferably somewhat beyond, the longitudinal axis 78. The extension of the helical excising finger 70 at least to the longitudinal axis 78 will enable the helical excising finger 70 to completely excise a biopsy sample from the lesion 24 when the coring cannula 16 is rotated. Alternatively, the helical excising finger 70 can extend just short of the longitudinal axis 78 so that a portion of the biopsy sample remains connected to the lesion 24. In such a configuration, care must be taken to ensure that the suction and/or frictional force acting on the biopsy sample in the core biopsy device 10, along with interference from the helical excising finger 70 on the sample, will exert sufficient force to retain the biopsy sample in the device 10 and separate the remainder of the biopsy sample from the tissue mass 22 as the device 10 is removed.

Referring to FIGS. 3 and 8A-C, the cannula assembly 14 is assembled by installing the stylet 20 into the lumen 56 of the spoon cannula 18, and installing the spoon cannula 18 into the lumen 76 of the coring cannula 16, to provide a telescoping assembly wherein the coring cannula 16 is slidably and coaxially disposed around the spoon cannula 18, which is slidably and coaxially disposed around the stylet 20. FIGS. 8A-C illustrate the various relative positions of the elements of the cannula assembly when it is moved from the cocked position (FIG. 8A) to an excising position (FIG. 8C).

As illustrated in FIG. 8A, when the cannula assembly 14 is operably attached to the actuator assembly 12 and placed in a cocked configuration, the penetration tip 34 of the stylet 20 extends somewhat distally of the insertion tip 48 of the spoon cannula 18. The insertion tip 48 also extends somewhat distally of the cutting tip 64 of the coring cannula 16 so that the distal edge 73 of the helical excising finger 70 is in resilient contact with the arcuate wall 46 of the spoon cannula 18, deflected away from the longitudinal axis 78.

FIG. 8B illustrates the cannula assembly 14 in an intermediate position between the cocked and excising positions. To achieve the intermediate position, after the cannula assembly 14 has been inserted into the tissue mass 22 to the lesion 24, the cannulae 16, 18 can be moved relative to the stylet 20 such that the distal ends of the cannulae 16, 18 extend beyond the penetration tip 34 of the stylet 20 with the insertion tip 48 of the spoon cannula 18 remaining extended distally of the helical excising finger 70 of the coring cannula 16. This intermediate position can be either a static or dynamic position. It is preferred that this is a dynamic position that is reached as part of the overall movement from the cocked to the excising position.

As illustrated in FIG. 8C, the coring cannula 16 is projected distally of the spoon cannula 18 so that the helical excising finger 70 extends distally of the insertion tip 48 to deflect toward the longitudinal axis 78. This configuration is referred to herein as the excising position. While in the excising position, the rotation of the coring cannula 16 and the helical excising finger 70 relative to the biopsy sample excises the sample from the tissue mass 22.

Referring again to FIG. 8A, as described above with respect to FIG. 7A, the configuration of the spoon cannula 18 comprising the elimination of a portion of the annular wall 44 to form the spoon section 42 results in the semi-annular gap 80 between the stylet 20 and the annular wall 62 of the coring cannula 16 when the coring cannula 16 is extended over the stylet 20 distally of the annular wall 44. The gap 80 is approximately equal to the thickness of the annular wall 44, or, in a preferred embodiment, approximately 0.004 inch. It is contemplated that this space is insufficient in size for tissue to be received within the gap 80 during the insertion of the cannula assembly into the tissue mass. However, if tissue were received within the gap 80, it might negatively impact the performance of the biopsy device 10.

Figure 8D:
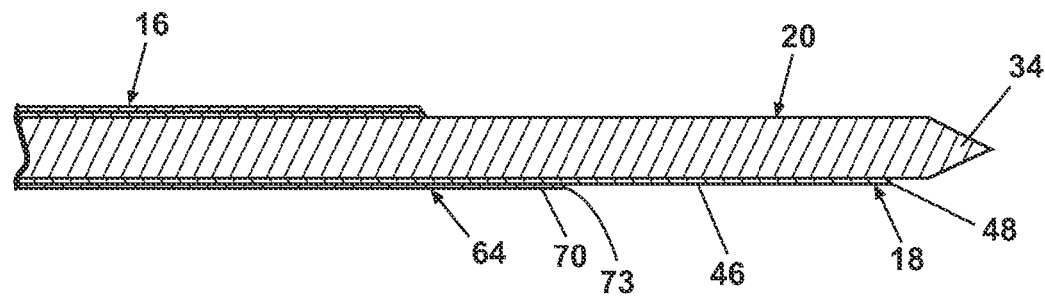
FIG. 8D is a longitudinal sectional view illustrating the cannula assembly in an alternative "cocked" configuration ready for insertion into the tissue mass.

FIG. 8D illustrates an alternate position of the coring cannula 16 in the "cocked" configuration that eliminates the gap 80 during the insertion of the cannula assembly into the tissue mass. As shown in FIG. 8D, the enclosed section 60 of the coring cannula 16 is coextensive with the enclosed section 40 of the spoon cannula 18, but does not extend distally beyond it. This configuration will enable the insertion of the cannula assembly 14 into the tissue mass 22 and the simultaneous advancement of the cannulae 16, 18 over the stylet 20 without the presence of a gap or interference from tissue drawn therein. Thus, the penetration tip 34 of the stylet 20 extends somewhat distally of the insertion tip 48 of the spoon cannula 18, but the insertion tip 48 does not extend distally of the cutting tip 64 of the coring cannula 16, which engages the spoon section 42 somewhat proximally of the insertion tip 48. The cannula assembly 14 is inserted into the tissue mass 22 so that the penetration tip 34 and the insertion tip 48 extend to the lesion 24. It will be recognized that the spoon section 42 will necessarily be of a sufficient strength to enable the spoon section 42 to penetrate the tissue mass 22 without deflection, which would be otherwise controlled by the envelopment of the spoon section 42 by the coring cannula 16.

Figure 9A:
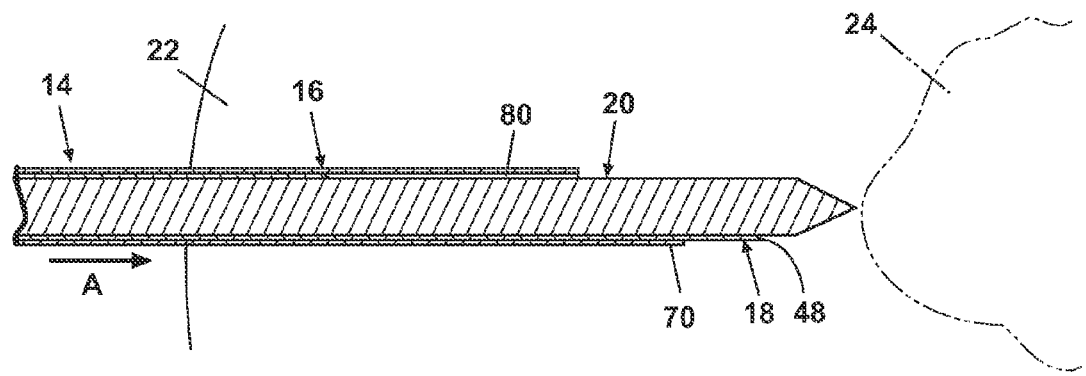
FIGS. 9A-G are longitudinal sectional view of the cannula assembly illustrated in FIG. 2 at various steps in the process of obtaining a core biopsy sample.

The operation of the core biopsy device 10 is illustrated in FIGS. 9A-F in the context of performing a breast biopsy. However, the core biopsy device 10 is not so limited, and can be utilized to obtain a core biopsy sample from other soft tissues, for example the liver, kidney, or skeletal muscles. As illustrated in FIG. 9A, the biopsy procedure is preferably initiated with the cannula assembly 14 in the cocked configuration. In this configuration, the cannula assembly 14 is inserted into the tissue mass 22 by manual or automated means. Preferably, the user grasps the actuator assembly 12 and inserts the cannula assembly 14 into the tissue mass 22 in the direction of arrow "A" using an imaging system to guide the positioning of the cannula assembly 14. Generally, the cannula assembly 14 is positioned within the tissue mass 22 such that, when the sample is taken, at least part of the lesion 24 is included in the sample.

Any suitable imaging system can be used, for example radiography, ultrasound, or MRI. As is well known in the art, the tip of the stylet, cannula, or spoon cannula can be made from material, shaped or provided with markings that enhance the visibility of the elements with a particular imaging system.

The penetration tip 34 of the stylet 20 extends somewhat distally of the insertion tip 48 of the spoon cannula 18 and the insertion tip 48 extends somewhat distally of the helical excising finger 70 to form a generally solid penetrating tip that facilitates the insertion of the cannula assembly 14 into the tissue mass 22. Portions of the cannula assembly 14 are preferably made such that they are easily viewable and positionable using the selected imaging technique.

Figure 9B:
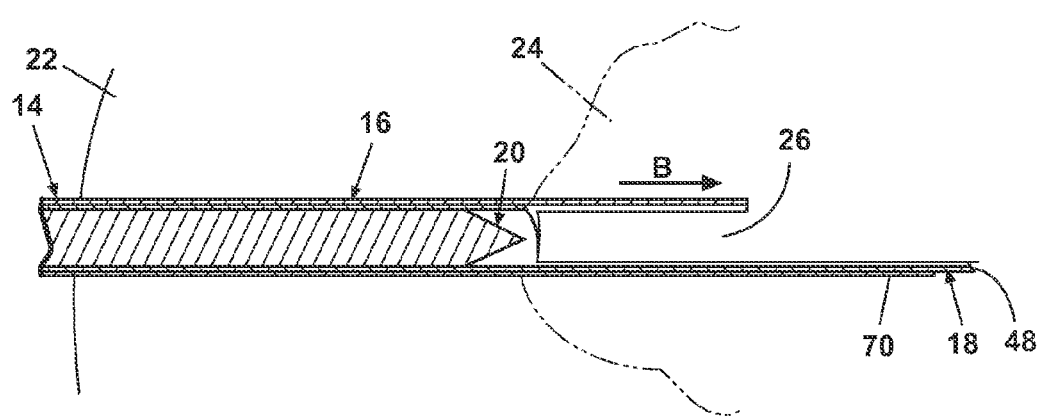

Referring to FIG. 9B, after the initial positioning of the cannula assembly 14, the cannula assembly is moved from the cocked to the excising condition. As part of this movement, the cannula assembly passes through the intermediate position. To affect this movement, the coring cannula 16 and the spoon cannula 18 are advanced relative to the stylet 20, preferably by axially sliding the coring cannula 16 and spoon cannula 18 in the direction of the arrow "B" along the stylet 20 and into the lesion 24 a distance predetermined by the desired length of the biopsy sample through activation of the actuator assembly 12. In the intermediate position, the helical excising finger 70 still remains behind the distal end of the spoon and the sample 26 is being cored from the tissue mass 24.

Figure 9C:
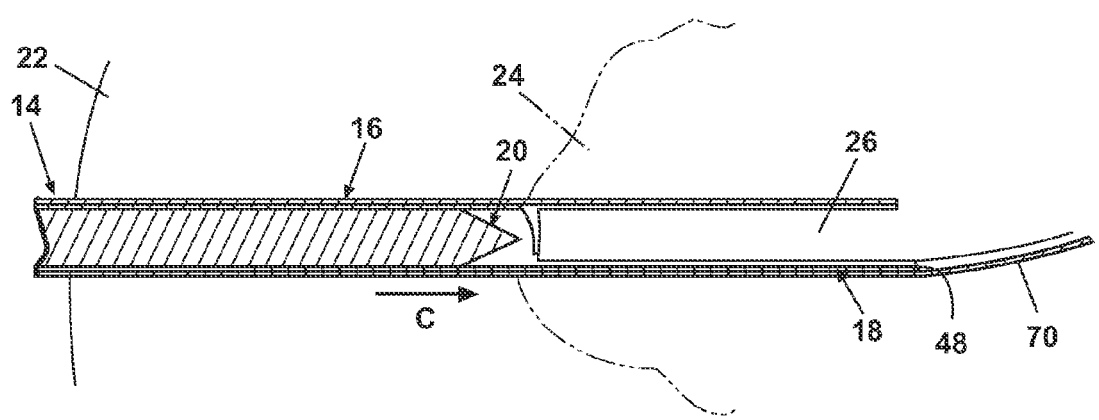

As illustrated in FIG. 9C, after the partial creation of the sample 26 with its end still connected to the tissue mass 22, the coring cannula 16 is advanced to the excising position to complete the coring of the sample 26. In the excising position, the helical excising finger 70 extends beyond the distal end of the spoon section 42 and into the end of the sample 26. This movement is accomplished by moving the coring cannula 16 in the direction of the arrow "C". As the helical excising finger 70 extends beyond the insertion tip 48, the inherent resilience and memory of the helical excising finger 70 causes it to resiliently return to its at-rest arcuate position, biased in the lesion 24 toward the longitudinal axis 78.

The advancement of the coring cannula 16 to the excising position can be done as part of or separate from the initial advancement of the coring cannula 16 and the spoon cannula 18. Preferably, the advancement of the coring cannula 16 is accomplished in the same step as the advancement of the spoon cannula 18 to form the sample core. To accomplish such a motion, the advancement of the spoon cannula 18 can be stopped prior to the advancement of the coring cannula 16. In other words, the spoon cannula 18 would have a shorter throw distance than the coring cannula 16.

Figure 9D:
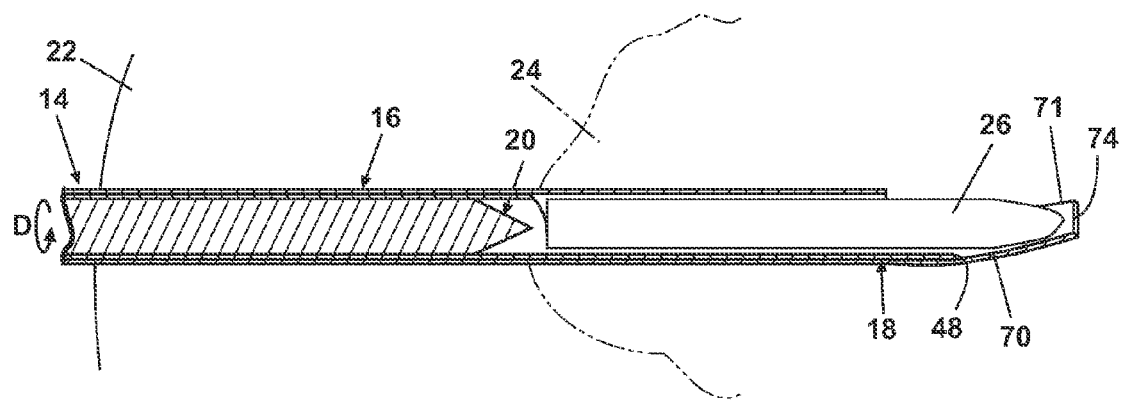
Figure 9F:
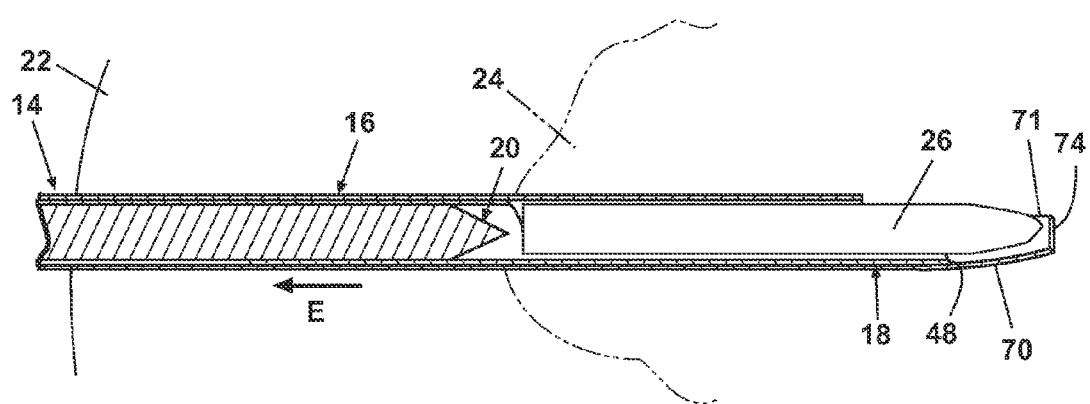
Figure 9G:
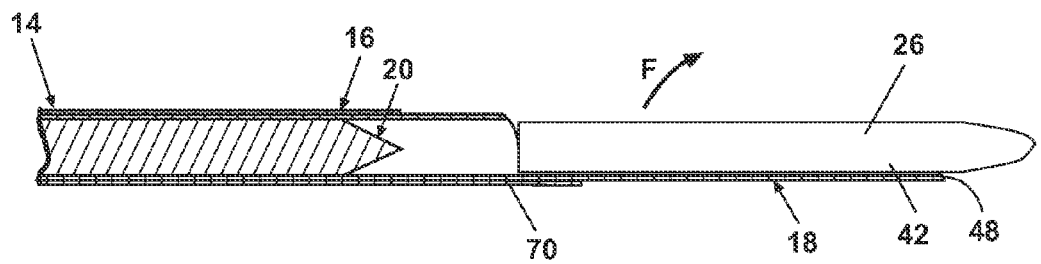
Figure 9E:
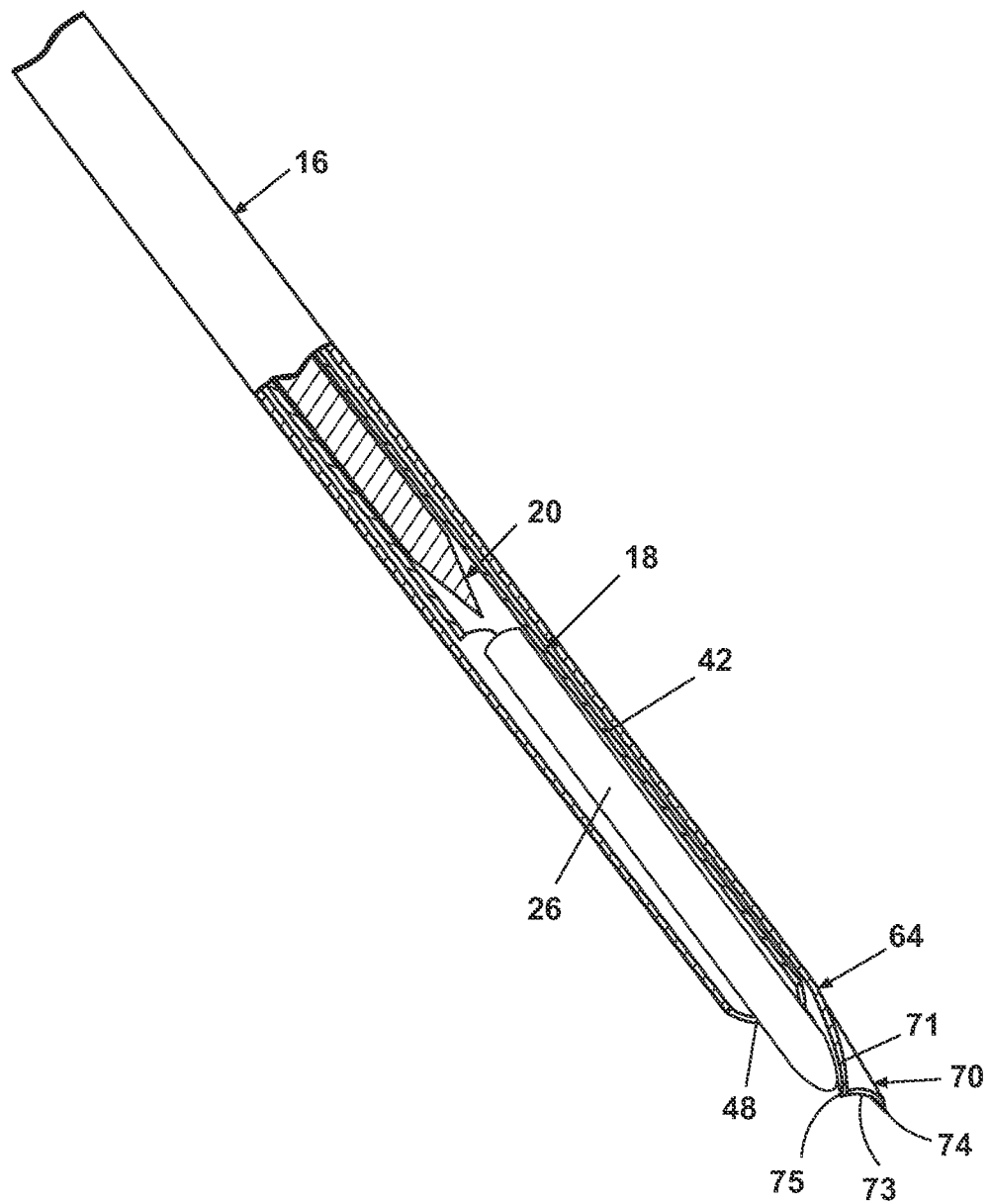

Referring to FIGS. 9D-E, with the coring cannula 16 in the excising position, the sample 26 is severed from the surrounding tissue mass by rotating the coring cannula 16 relative to the spoon cannula 18. Rotation of the coring cannula 16 excises the biopsy sample 26 from the lesion 24 by the cutting action of one of the lateral edges 71, 72 and one of the corners 74, 75. When rotated counterclockwise, when viewed from the proximal end, the corner 74 acts as an excising tip and the lateral edge 71, lead by the corner 74, acts as an excising edge. The excising tip or corner 74 leads the excising edge or lateral edge 74 in cutting the biopsy sample 26 from the surrounding tissue. It is also contemplated that the coring cannula 16 can be rotated clockwise when viewed from the proximal end. Therefore, the corner 75 would act as the excising tip and the lateral edge 72 would act as the excising edge.

As illustrated in FIG. 9D, the coring cannula is rotated in the direction of arrow "D", which is counterclockwise when viewed from the proximal end of the cannula assembly 14. The rotation of the helical excising finger 70 causes the lateral edge 71, acting as the excising edge, and the corner 74, acting as the excising tip, to sever the end of the sample 26 from the tissue mass 22 to form a somewhat rounded conical surface at the distal end of the biopsy sample 26. The helical excising finger 70 can be rotated approximately 360 degrees to ensure that the biopsy sample 26 has been completely excised from the lesion 24. However, the rotation need only be sufficient to ensure the separation of the sample 26 from the tissue mass 22, which can include a partial revolution or multiple revolutions.

Referring to FIG. 9F, after excising the biopsy sample 26 from the lesion 24, the cylindrical biopsy sample 26 will be supported by the spoon section 42 within the lumen 76, held in place partly by the friction of the cylindrical surface of the sample 26 against the arcuate wall 46 and the annular wall 62, and the helical excising finger 70. With this configuration, the sample 26 is retained within the coring cannula 16 upon removal from the tissue mass 22 by withdrawing the cannula assembly 14 in the direction of arrow "E".

Referring to FIG. 9G, after the cannula assembly 14 is withdrawn from the tissue mass 22, the biopsy sample 26 is removed from the core biopsy device 10 by relatively moving the coring cannula 16 and the spoon cannula 18 such that the spoon section 42 extends beyond the cutting tip 64 of the coring cannula 16. In this position, the sample 26 extends beyond the coring cannula 16 while still being supported by the spoon section 42. The helical excising finger 70 is also located behind the distal end of the spoon section 42. The practitioner can then lift the sample 26 away from the spoon section 42, as indicated by arrow "F". This is a great advantage over prior art full core biopsy devices that use the advancement of the stylet to expel the sample. The forced expulsion of the sample can damage the sample and in some cases can render the sample unusable. The biopsy device 10 of the invention can be configured to advance the stylet 20 to expel the sample 26 as do the prior art devices, but for the reasons just stated, it is highly undesirable.

The core biopsy device 10 described herein provides several distinct advantages over the prior are which increase the probability of obtaining a high-quality biopsy sample. The use of the rotational cutting mechanism ensures that the sample is completely excised from the surrounding tissue mass, thereby minimizing the potential for disturbance or degradation of the sample when pulling the sample away from the tissue mass in order to sever it. This also minimizes the potential that the sample will separate from the tissue mass at a location within the sample itself rather than at its attachment to the tissue mass, thereby avoiding a sample volume which is inadequate for analysis.

The helical shape of the helical excising finger 70 offers a cutting advantage over other excising fingers having a curved or arcuate shape such as the excising finger disclosed in U.S. patent application Ser. No. 10/908,427, filed May 11, 2005, now U.S. Pat. No. 8,088,081, issued Jan. 3, 2012. In the case of arcuate excising fingers, substantially the entire lateral edge of the excising finger is normal to the direction of rotation. The rotational force associated with an arcuate excising finger is then spread across the lateral edge. The rotational force must be great enough to push the edge of the arcuate excising finger through the tissue mass.

In contrast, the corner 74 of the helical excising finger 70 forms a leading tip or point that is oriented with the direction of rotation and begins the cutting of the tissue when the coring cannula 16 is rotated counterclockwise, begins cutting. Since the point as the corner 74 has a smaller area than the following edge 71, a greater pressure will be generated at the point for a given rotational force, which will provide cleaner severing of the tissue instead of tearing of the tissue as compared to an arcuate excising finger. The greater pressure at the point can be thought of as concentrating the force at the corner 74, making the initial penetration cut is easier. Through continued rotation of the coring cannula 16, the excising tip leads the excising edge, which is lateral edge 71, through the tissue and provides the lateral edge with and exposed and clean cut surface against which to cut. The helical curvature of the lateral edge 71 allows the helical excising finger 70 to slice more efficiently through tissue and will generate less tearing of the tissue and encounter less resistance than an arcuate excising finger.

Additionally, the use of a spoon-shaped biopsy sample support minimizes the disturbance and degradation of the sample which can occur with devices having enclosed sample chambers requiring the sample be ejected by a plunger, the stylet, or similar means. This avoids the necessity of obtaining a second sample if the first one proves to be unusable.

Finally, the core biopsy device 10 can be inserted, cocked, and actuated by an operator using one hand, thereby enabling the operator to concurrently operate an imaging device, such as an ultrasound wand, for positioning the cannula assembly 14, eliminating the need for an additional imaging technician. Thus, the core biopsy device 10 is easily inserted and triggered with one hand, providing very quick recovery of a biopsy sample, thereby enhancing the quality of the biopsy sample and minimizing discomfort to the patient.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention, which is defined in the appended claims.

What is claimed is:

1. A biopsy apparatus for percutaneous removal of a specimen from a tissue mass, the biopsy apparatus comprising:
    a cannula defining a lumen and a longitudinal axis, the cannula having a proximal end, a distal end terminating in a beveled edge, and a helical excising finger extending from the distal end beyond the beveled edge; and
    an actuator operably coupled to the cannula and configured to axially move, without rotating, the cannula from an inserting position to an excising position, and to rotate the excising finger about the longitudinal axis when the cannula is in the excising position;
    wherein the helical excising finger comprises a lateral excising edge configured to at least partially sever the specimen from the tissue mass as the cannula is rotated by the actuator; and
    wherein the helical excising finger comprises a distal excising tip configured to, as the cannula is rotated by the actuator, lead the excising edge through the tissue mass and to aid in at least partially severing the specimen from the tissue mass.

2. The biopsy apparatus according to claim 1, and further comprising an inner cannula received within the lumen, the inner cannula having a proximal end and a distal end.

3. The biopsy apparatus according to claim 2, wherein the actuator is configured to axially move the cannula relative to the inner cannula from the inserting position to the excising position where the helical excising finger extends distally of the distal end of the inner cannula.

4. The biopsy apparatus according to claim 3, wherein the inner cannula comprises a spoon portion that terminates at the distal end for supporting a biopsy sample.

5. The biopsy apparatus according to claim 4, and further comprising a stylet received within the inner cannula to substantially close off the inner cannula in the inserting position.

6. The biopsy apparatus according to claim 5, wherein the actuator axially advances the cannula relative to the stylet when moving the cannula to the excising position to form a tissue receiving area between the distal end of the cannula and the stylet.

7. The biopsy apparatus according to claim 6, wherein a position of the stylet is adjustable relative to the excising position of the cannula to provide for adjusting a length of the tissue receiving area.

8. The biopsy apparatus according to claim 1, wherein the actuator and cannula collectively define an integrated self-contained hand-holdable device that can be handled by a user to effect operation of the biopsy apparatus.

9. The biopsy apparatus according to claim 1, wherein the excising tip comprises a corner which forms a leading tip that is oriented with the direction of rotation, and wherein the leading tip begins cutting tissue when the cannula is rotated in the direction of rotation.

10. A biopsy apparatus for percutaneous removal of a core specimen from a tissue mass, the biopsy apparatus comprising:
    a cannula defining a lumen and a longitudinal axis, the cannula having a proximal end, a distal end terminating in a beveled edge, and a helical excising finger extending from the distal end beyond the beveled edge;
    a stylet received within the lumen, the stylet having a distal end; and
    an actuator operably coupled to the cannula for axially moving the cannula relative to the stylet to partially form a core specimen having an end attached to the tissue mass, and for rotating the cannula about the longitudinal axis with the helical excising finger in an excising position, in which the helical excising finger extends beyond the distal end of the stylet into the end of the core specimen attached to the tissue mass to sever the core specimen from the tissue mass;
    wherein the excising finger is configured for resilient flexure between a first position generally parallel to the longitudinal axis and the excising position, such that when the excising finger extends beyond the distal end of the stylet, the excising finger flexes toward the longitudinal axis;
    wherein the helical excising finger comprises a lateral excising edge configured to at least partially sever the specimen from the tissue mass as the cannula is rotated by the actuator; and
    wherein the helical excising finger comprises a distal excising tip configured to, as the cannula is rotated by the actuator, lead the excising edge through the tissue mass and to aid in at least partially severing the specimen from the tissue mass.

11. The biopsy apparatus according to claim 10, where the actuator is configured to axially move the cannula relative to the stylet prior to rotating the cannula.

12. The biopsy apparatus according to claim 10, and further comprising an inner cannula received within the lumen, the inner cannula terminating in a spoon portion for supporting a biopsy sample.

13. The biopsy apparatus according to claim 10, wherein the actuator and cannula collectively define an integrated self-contained hand-holdable device that can be handled by a user to effect operation of the biopsy apparatus.

14. The biopsy apparatus according to claim 10, wherein the excising tip comprises a corner which forms a leading tip that is oriented with the direction of rotation, and wherein the leading tip begins cutting tissue when the cannula is rotated in the direction of rotation.

15. A biopsy apparatus for percutaneous removal of a specimen from a tissue mass, the biopsy apparatus comprising:
    a cannula defining a lumen and a longitudinal axis, the cannula having a proximal end and a distal end;
    an actuator operably coupled to the cannula for rotating the cannula about the longitudinal axis in a direction of rotation; and
    an excising finger extending beyond the distal end of the cannula and having a sharpened excising tip oriented in the direction of rotation of the cannula so that the rotation will cause the excising tip to lead an adjacent lateral edge through the tissue;

wherein the excising finger is configured for resilient flexure between a first position generally parallel to the longitudinal axis and a second position toward the longitudinal axis.

16. The biopsy apparatus according to claim 15, wherein the excising finger is attached at and extends from the distal end of the cannula.

17. The biopsy apparatus according to claim 16, wherein the lateral edge extends from the distal end of the cannula to the excising tip.

18. The biopsy apparatus according to claim 17, wherein the lateral edge is helical in at least the second position.

19. The biopsy apparatus according to claim 18, wherein the excising tip comprises a corner which forms a leading tip that is oriented with the direction of rotation, and wherein the leading tip begins cutting tissue when the cannula is rotated in the direction of rotation.

20. The biopsy apparatus according to claim 15, wherein the actuator and cannula collectively define an integrated self-contained hand-holdable device that can be handled by a user to effect operation of the biopsy apparatus.

21. The biopsy apparatus according to claim 15, and further comprising a stylet received within the lumen.

22. The biopsy apparatus according to claim 15, and further comprising a spoon cannula received within the lumen, wherein the spoon cannula comprises a spoon portion that terminates at a distal end of the spoon cannula for supporting the specimen.

* * * * *